United States Patent [19]

Honma et al.

[11] Patent Number: 4,695,734
[45] Date of Patent: Sep. 22, 1987

[54] PHOTOELECTRIC SMOKE SENSOR INCLUDING A PHOTOSENSING DATA CORRECTION RATIO CORRECTION CIRCUIT

[75] Inventors: Hiroshi Honma, Tokyo; Junichi Narumiya, Kanagawa, both of Japan

[73] Assignee: Hochiki Corporation, Tokyo, Japan

[21] Appl. No.: 703,385

[22] Filed: Feb. 20, 1985

[30] Foreign Application Priority Data

Mar. 5, 1984 [JP] Japan ............................. 59-31476[U]

[51] Int. Cl.⁴ ...................... G01N 15/06; G08B 17/10
[52] U.S. Cl. ...................................... 250/573; 340/630
[58] Field of Search ........................ 250/573, 574, 575; 340/630; 356/438, 439, 436, 437

[56] References Cited

U.S. PATENT DOCUMENTS

| | | | |
|---|---|---|---|
| 3,982,130 | 9/1976 | Trumble | 356/439 |
| 4,300,133 | 11/1981 | Solomon | 250/574 |
| 4,308,531 | 12/1981 | Yamamoto | 250/573 |
| 4,420,746 | 12/1983 | Malinowski | 250/574 |
| 4,547,675 | 10/1985 | Muggli et al. | 250/575 |
| 4,556,873 | 12/1985 | Yamada et al. | 250/574 |

Primary Examiner—David C. Nelms
Assistant Examiner—William L. Oen
Attorney, Agent, or Firm—Wenderoth, Lind & Ponack

[57] ABSTRACT

A light emitting unit and a photo sensing unit are separately arranged to face with each other, and a pulse light is emitted from the light emitting unit at every constant period, and the photo sensing unit receives the pulse light attenuated by a smoke, thereby detecting a fire. When a power source is turned on, a microcomputer in the photo sensing unit stores the first photo sensing data as an initial photo sensing data in a memory. The initial photo sensing data is fixedly stored and held and is not erased due to a temporary cut off of the power source. The photo sensing data is converted to correction photo sensing data using a correction ratio to perform the fouling correction and the fire is discriminated on the basis of the correction photo sensing data. The correction ratio is corrected when the correction period reaches 50 minutes. A correction amount of a single correction ratio is suppressed to a microvalue. In correction of the correction ratio, it is increased or decreased by only a microvalue at every correction period until the photo sensing data coincides with the initial photo sensing data.

5 Claims, 6 Drawing Figures

PHOTOELECTRIC SMOKE SENSOR INCLUDING A PHOTOSENSING DATA CORRECTION RATIO CORRECTION CIRCUIT

BACKGROUND OF THE INVENTION

The present invention relates to a photoelectric smoke sensor in which light emitting units and photo sensing units are arranged to face with each other with a constant distance apart from each other and the occurrence of fire is detected on the basis of attenuation of the light due to the smoke flowed into the area between the light emitting and photo sensing units installed and, more particularly, to a photoelectric smoke sensor in which a variation in photo sensing signal due to a fouling of the optical system is corrected.

Hitherto, in photoelectric smoke sensors in which light emitting units and photo sensing units are arranged to face with each other, with an elapse of a long use time, the dust is deposited on the windows of the light emitting and photo sensing units, so that a level of the photo sensing signal decreases and if the photo sensing signal level decreased due to the dust becomes a level below a threshold value at which it is determined that the fire occurred, an error fire signal will have been outputted. Therefore, it is necessary to perform the cleaning work to remove the dust at every constant period.

However, since the cleaning work for removal of the dust is troublesome, an apparatus in which the photo sensing signal is automatically corrected in accordance with a degree of deposition of the dust has been considered. For example, a photoelectric smoke sensor disclosed in U.S. Pat. Ser. No. 4,317,113 has been known.

In this photoelectric smoke sensor, a gain of an operational amplifier for amplifying a photo sensing signal is varied step by step in accordance with a degree of attenuation of the signal due to the deposition of the dust, and when the photo sensing signal attenuates due to the deposition of the dust, the amplification gain is increased by an amount as much as a degree of attenuation, thereby making it possible to obtain the photo sensing signal in the same condition as that whereby no dust is deposited.

However, the fouling correction by means of the gain control of the operational amplifier has the following problems.

(( The first problem ))

As a method of varying the amplification gain, an impedance of a resistance network provided in the feedback circuit of the operational amplifier is changed due to the on/off controls of a plurality of analog switches. However, analog switches generally have ON-state resistance of about 100 to 300 ohms and the feedback impedance cannot be accurately set due to the existence of this ON-state resistance, so that it is difficult to linearly control the gain by way of change-over of the switch.

(( The second problem ))

To realize the linearity of the gain control by the change-over of the switch, the impedances have to be controlled by providing a number of variable resistances, so that this causes the circuit to become complicated and the control operation to become troublesome as well.

(( The third problem ))

An up-down counter is needed for the on/off controls of a plurality of analog switches, so that there is a problem such that the gain control circuit becomes complicated.

On the other hand, in a method of correcting the fouling by way of the gain control, the initial photo sensing data and the present photo sensing data are compared at every constant period and the gain of the operational amplifier is varied on the basis of a difference between these data so as to cancel the difference. However, in the case where the smoke concentration gradually increases such as a fumigation fire, such a signal reduction is also corrected by the control of the amplification gain, so that there is a risk such that the fire cannot be detected.

In addition, since the initial photo sensing data for the fouling correction is stored when the power source is turned on, for instance, after a fire signal was outputted to a receiver due to the detection of the smoke, even when the power source is once turned off for recovery and then it is again turned on, the photo sensing data decreased due to the smoke at that time is newly stored as an initial photo sensing data, so that there is a risk such that the fire after the recovery cannot be detected.

Further, in the case where the initial photo sensing data stored due to the turning-on of the power source is abnormal, the threshold value of the fire determination which is set on the basis of the initial photo sensing data also becomes abnormal; consequently, there is a risk that an error alarm or wrong alarm is generated.

SUMMARY OF THE INVENTION

It is an object of the present invention to provide a photoelectric smoke sensor in which photo sensing data is inputted as it is without being corrected and the correction photo sensing data is obtained from the calculating process based on the correction coefficient at that time.

Another object of the invention is to provide a photoelectric smoke sensor in which the initial photo sensing data derived when a power source is first turned on is stored and upon fouling correction which is performed at every predetermined period, a correction ratio is corrected in accordance with a difference between the initial photo sensing data and the present photo sensing data, and the correction photo sensing data is obtained due to a multiplication of the present photo sensing data by that correction ratio.

Still another object of the invention is to provide a photoelectric smoke sensor in which when a difference is caused between the initial photo sensing data and the present photo sensing data, the correction ratio is corrected by only an amount as much as a predetermined microvalue.

Still another object of the invention is to provide a photoelectric smoke sensor in which the initial photo sensing data can be held stored for a constant time interval even after the power source was turned off. Still another object of the invention is to provide a photoelectric smoke sensor in which a storage of abnormal data is prevented by checking the initial photo sensing data which is stored to see if it lies within a predetermined range or not.

These and other objects, features and advantages of the invention will become apparent from the following

DESCRIPTION OF PREFERRED EMBODIMENT

Figure 1:
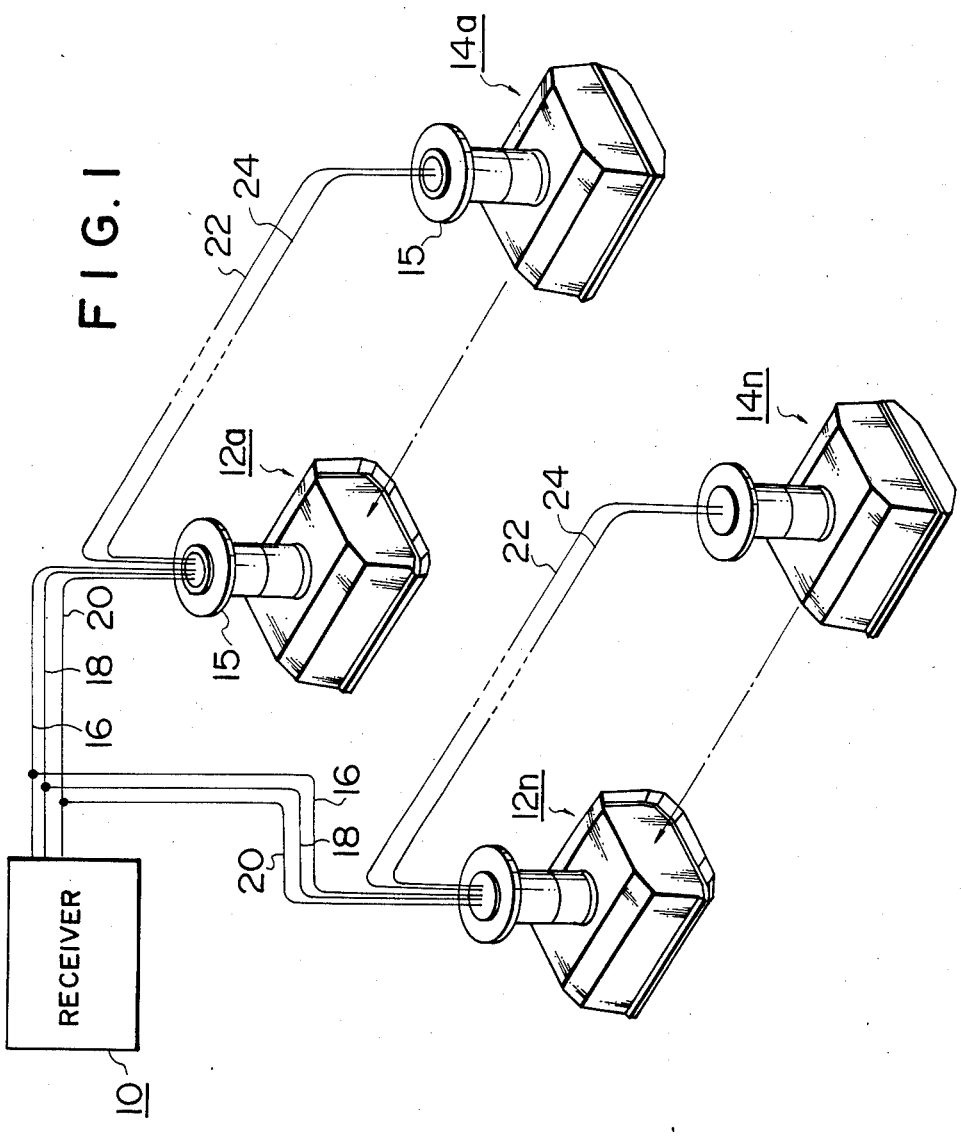
FIG. 1 is an explanatory diagram showing one embodiment of an arrangement of a system of the present invention.

FIG. 1 is an explanatory diagram showing one embodiment of the overall arrangement of the present invention as a photoelectric smoke sensor of the extinction separation type.

In FIG. 1, a reference numeral 10 denotes a receiver which is installed in a central monitor room or the like. The receiver 10 receives a fire detection signal from a photoelectric smoke sensor and generates a fire alarm and simultaneously displays the district where the fire occurred. The receiver 10 also receives an inspection alarm signal when a trouble occurs in a photoelectric smoke sensor and Performs an alarm indication to allow the photoelectric smoke sensor to be inspected. A signal line 16, which also serves as a power source, an inspection signal line 18 and a common line 20 are drawn out from the receiver 10. Photo sensing units 12a, . . . , 12n in a plurality of photoelectric smoke sensors are connected to those signal lines 16, 18 and 20.

In the photoelectric smoke sensor of the present invention, a single photoelectric smoke sensor is constituted by a combination of the photo sensing unit 12a and a light emitting unit 14a, or by a combination of the photo sensing unit 12n and a light emitting unit 14n, respectively.

For instance, an explanation will be made with respect to a single photoelectric smoke sensor consisting of the photo sensing unit 12a and the light emitting unit 14a. In this case, the light emitting unit 14a is arranged to face the photo sensing unit 12a with a predetermined distance within a range of 5 to 100 m, e.g., a distance of 15 m. A pair of signal lines 22 and 24 are drawn out from the photo sensing unit 12a and are connected to the light emitting unit 14a. This connection of the signal lines 22 and 24 is also the same as that of the photo sensing unit 12n and light emitting unit 14n. Further, the respective photo sensing units 12a, . . . , 12n and light emitting units 14a, . . . , 14n constituting the photoelectric smoke sensors are attached to a ceiling surface or the like through an attaching base 15, respectively.

Figure 2:
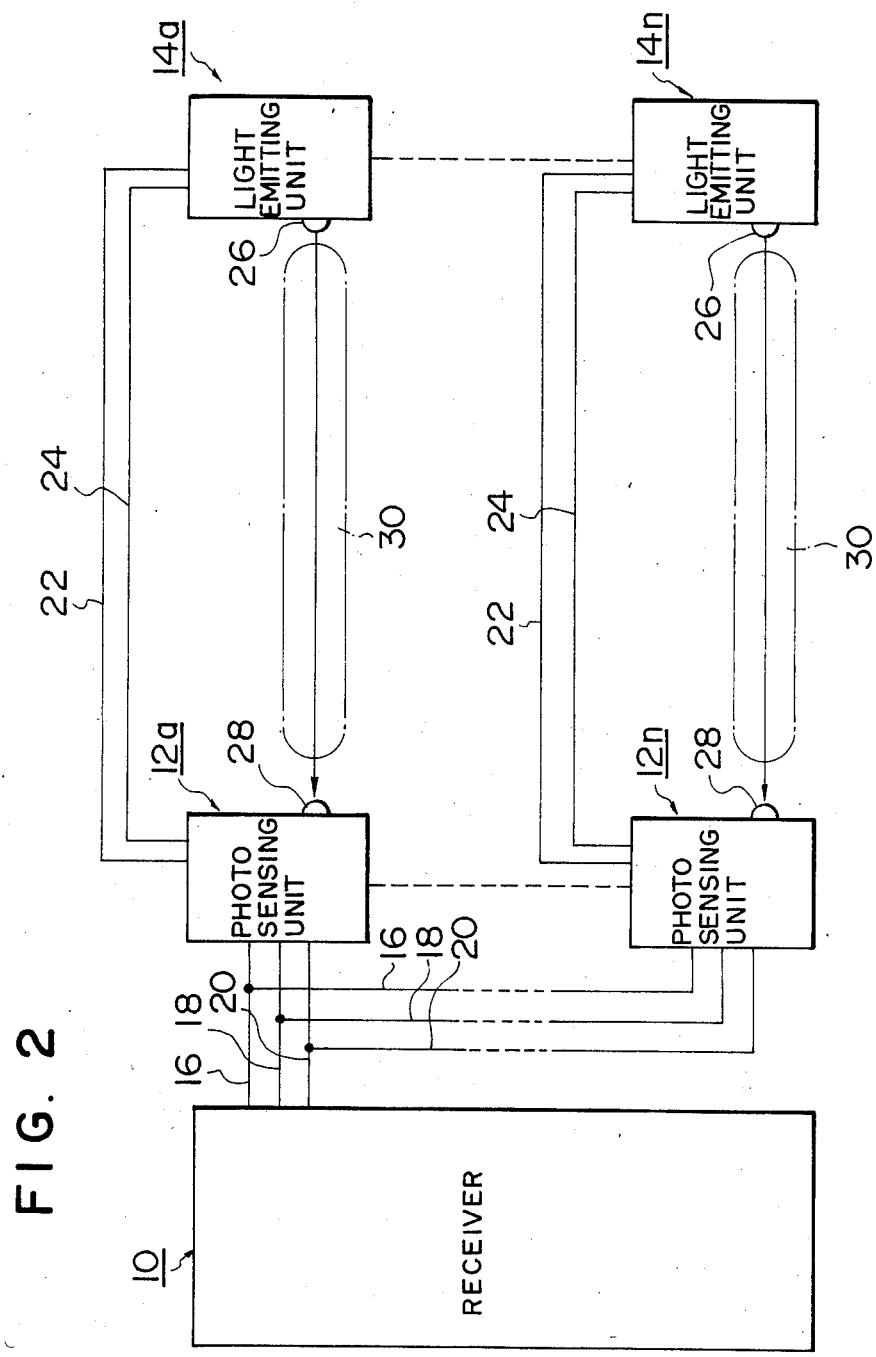
FIG. 2 is a block diagram showing an arrangement of the system of the invention.

FIG. 2 is a block diagram showing an arrangement of the system of FIG. 1, in which the photo sensing unit 12a and light emitting unit 14a, and the photo sensing unit 12n and light emitting unit 14n are arranged to face with each other with a predetermined distance, respectively. Light emitting elements 26 are provided for the light emitting units 14a and 14n. Light emission control signals are transmitted from the photo sensing units 12a and 12n to the light emitting elements 26 through the signal lines 22 and 24, which also serve as power supply lines, so that the light emission of the light emitting elements 26 is driven. The lights from the light emitting elements 26 enter photo sensing elements 28 provided for the photo sensing units 12a and 12n through smoke detecting regions 30. Therefore, when attaching the photo sensing unit 12a and light emitting unit 14a, or the photo sensing unit 12n and light emitting unit 14n onto the surface of the ceiling or the like, the optical axis is adjusted so that the light from the light emitting element 26 accurately enters the photo sensing element 28. On one hand, the light which is emitted from the light emitting element 26 and passes through the smoke detecting region 30 and enters the photo sensing element 28 is subjected to attenuation due to the smoke existing in the smoke detecting region 30. Thus, the light of the intensity attenuated in dependence upon the smoke concentration is inputted to the photo sensing element 28.

A control section using a microcomputer is built in each of the photo sensing units 12a and 12n, respectively. The initial power source after the adjustment of installation with regard to the optical axis or the like and the photo sensing data which is derived when the power source is turned on are stored as initial photo sensing data in a memory of the microcomputer. The threshold value at which it is determined that the fire occurred is operated on the basis of the initial photo sensing data stored in the memory. Whenever the photo sensing data is obtained, it is compared with the threshold level to discriminate the occurrence of fire. When it is decided that the fire occurred, a fire signal is transmitted to the receiver 10 through the signal line 16, which also serves as the power source. In addition, as will be clearly explained later, the initial photo sensing data stored in the memory of the microcomputer is used in the control process for a fouling correction. When the initial photo sensing data exceeds the correction limit in the control process for the fouling correction, an inspection alarm signal to indicate that the fouling correction reaches the limit is outputted to the receiver 10 through the inspection signal line 18. Further, in the case where the initial photo sensing data which is stored in the memory when the power source is first turned on is abnormal, the inspection signal line 18 also transmits an alarm signal for inspection to the receiver 10.

Figure 3:
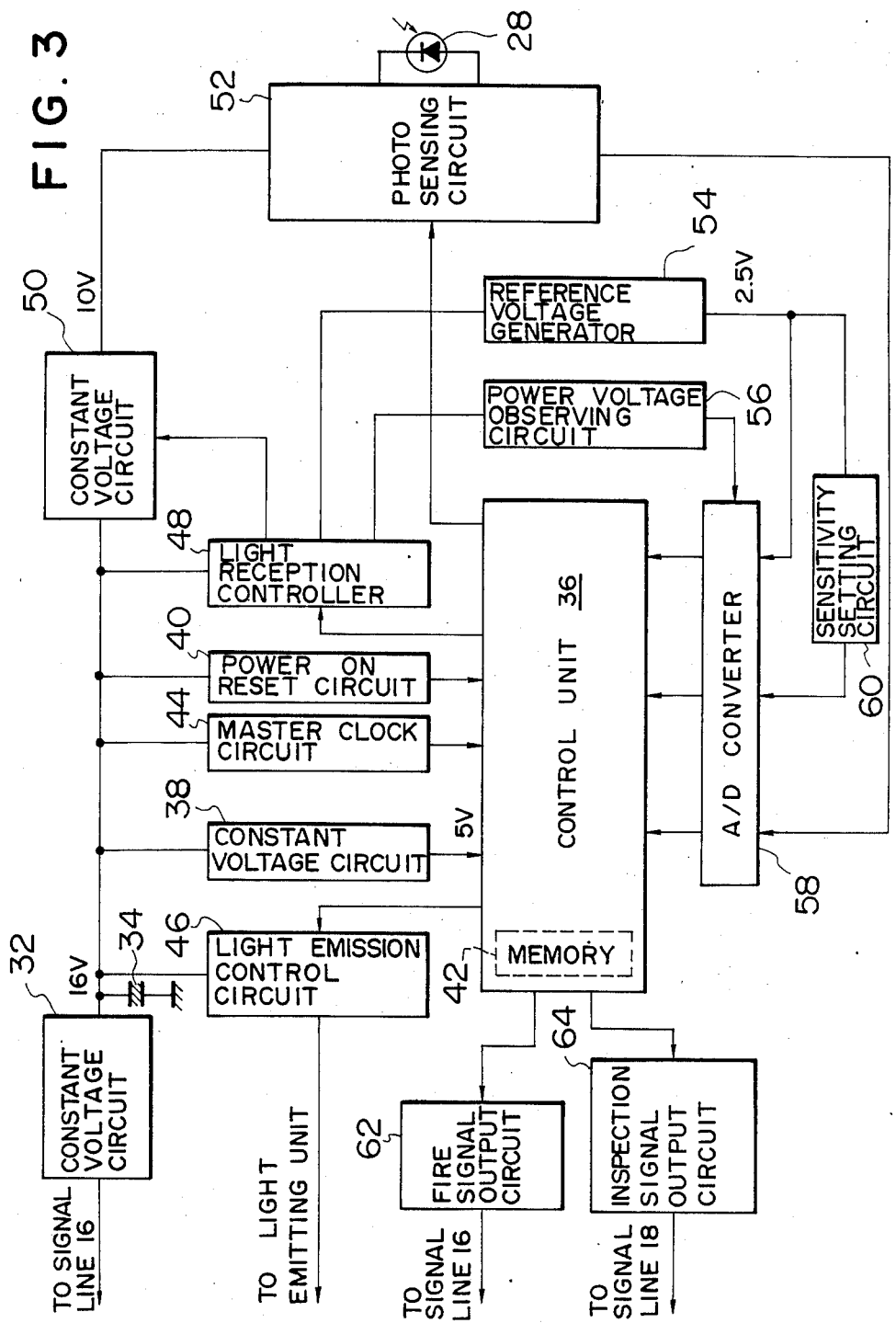
FIG. 3 is a block diagram showing one embodiment of a receiving unit of the invention.

FIG. 3 is a block diagram showing a circuit arrangement of the photo sensing unit for use in the photoelectric smoke sensor of the present invention using the microcomputer as the control section.

In FIG. 3, a constant voltage circuit 32 receives a power supply from the receiver and outputs a power source voltage of, e.g., 16 V. A capacitor 34 of a large capacitance is connected to an output of the constant voltage circuit 32. Even if the power supply from the receiver is temporarily cut off due to a power failure or the like, the power source is supplied to the microcomputer as the control section for a constant time interval due to the voltage charged in the capacitor 34, thereby making it possible to hold the storage of the initial photo sensing data $D_i$ to be stored in the memory of the microcomputer. Consequently, even if the power supply from the receiver is temporarily cut off, the initial photo sensing data $D_i$ will not be erased.

The capacitor 34 also has a function to smooth the output voltage from the constant voltage circuit 32.

A reference numeral 36 denotes a control unit using a microcomputer. For example, a microcomputer of eight bits is used and practically speaking, μPD80C48C made by Nippon Electric Co., Ltd. is used. The power supply to the control unit 36 using the microcomputer is performed by a constant voltage circuit 38. The constant voltage circuit 38 converts the output voltage of 16 V from the constant voltage circuit 32 to a constant voltage of 5 V and supplies it to the control unit 36.

A power on reset circuit 40 is made operative when the power source is turned on and outputs an initial reset signal to start the microcomputer in the control unit 36. In response to this initial reset signal, the control unit 36 performs the light emission control and light reception control and allows the initial photo sensing data obtained due to the light emission and light reception controls immediately after the power source was turned on to be stored in a memory 42. When the initial photo sensing data is stored in the memory 42, a data check is made to see if the initial photo sensing data lies within a predetermined range or not. When it lies within this range, the initial photo sensing data is stored in the memory 42. On the contrary, when it is out of the range, an alarm signal for inspection is outputted to the receiver.

After completion of the storing process of the initial photo sensing data based on the output of the power on reset circuit 40 by turning on the power source, the microcomputer in the control unit 36 stops the program control and returns to the standby mode. The subsequent operations of the control unit 36 are performed in response to a clock pulse from a master clock circuit 44. The master clock circuit 44 outputs a clock pulse to the control unit 36 at every constant period within a range of 2 to 4 seconds. In response to this clock pulse, the control unit 36 executes the light emission and light reception controls and inputs the photo sensing data which is obtained at this time as it is and obtains the correction photo sensing data due to the operating process for the fouling correction, thereby discriminating the fire due to the comparison between the correction photo sensing data and the threshold value.

A light emission control unit 46 receives a light emission control signal which is outputted due to the operation of the control unit 36 immediately after the power source was turned on and based on the master clock and outputs a control signal to the light emitting unit, thereby pulse driving the light emitting element provided for the light emitting unit by use of a discharge of the capacitor. Due to this, the light to detect the smoke is emitted to the photo sensing unit. Similarly to the light emission control unit 46, a light reception control unit 48 operates in response to a light reception control signal from the control unit 36 which operated on the basis of the output of the power on reset circuit 40 immediately after the power source was turned on or on the basis of the clock pulse of the master clock circuit 40. Namely, the light reception control unit 48 makes a constant voltage circuit 50 operative, thereby supplying a power source voltage of 10 V to a photo sensing circuit 52. Also, the light reception control unit 48 makes a reference voltage generator 54 operative to generate a reference voltage of, e.g., 2.5 V for A/D conversion and further makes a power source voltage observing circuit 56 for observing the output voltage of the constant voltage circuit 32 operative.

The photo sensing circuit 52 includes the photo sensing element 28, amplifying circuit and peak hold circuit therein. This photo sensing circuit 52 receives the light emission from the light emitting unit by the photo sensing element 28 and converts it to an electrical signal and amplifies this photo sensing signal to a specified level by the amplifying circuit. At the same time, the photo sensing circuit 52 holds the peak level of the photo sensing signal by the peak hold circuit and outputs this signal. The photo sensing signal outputted from the photo sensing circuit 52 is supplied to an A/D converter 58 and is converted to the digital signal of, e.g., four bits and is inputted as the photo sensing data to the control unit 36. The A/D converter 58 converts the photo sensing signal from the photo sensing circuit 52 to the digital signal on the basis of the reference voltage of 2.5 V from the reference voltage generator 54. In addition, a sensitivity setting signal from a sensitivity setting circuit 60 is also inputted to the A/D converter 58. The sensitivity setting circuit 60 takes out the output voltage of the reference voltage generator 54 as a different divided voltage due to a change-over by a rotary switch or the like, thereby variably setting the threshold value for fire determination in the control unit 36. The sensitivity setting signal from the sensitivity setting circuit 60 is also converted to the digital signal by the A/D converter 58 and is supplied to the control unit 36. Further, the power source voltage observing circuit 56 observes the output voltage of 16 V of the constant voltage circuit 32. When the power source voltage drops to a level, e.g., below 12 V, the observing circuit 56 informs abnormality of the power source to the control unit 36 through the A/D converter 58.

A fire signal output circuit 62 receives an output which is generated when the control unit 36 determines the occurrence of fire and performs the switching operation and allows a fire signal current to flow between the signal line 16 also serving as the power source and common line 20 drawn out from the receiver 10, thereby transmitting the fire signal. When the photo sensing unit is determined to be abnormal by the control unit 36, an inspection signal output circuit 64 allows an inspection current to flow between the inspection signal line 18 and common line 20 drawn out from the receiver 10, thereby transmitting the inspection signal. The fire signal current by the fire signal output circuit 62 and the inspection signal current by the inspection signal output circuit 64 become, e.g., up to 30 milliamperes, respectively. On the other hand, in the state whereby the fire signal or inspection signal is not outputted, those currents are suppressed to an average observing current of about 250 microamperes.

Figure 4:
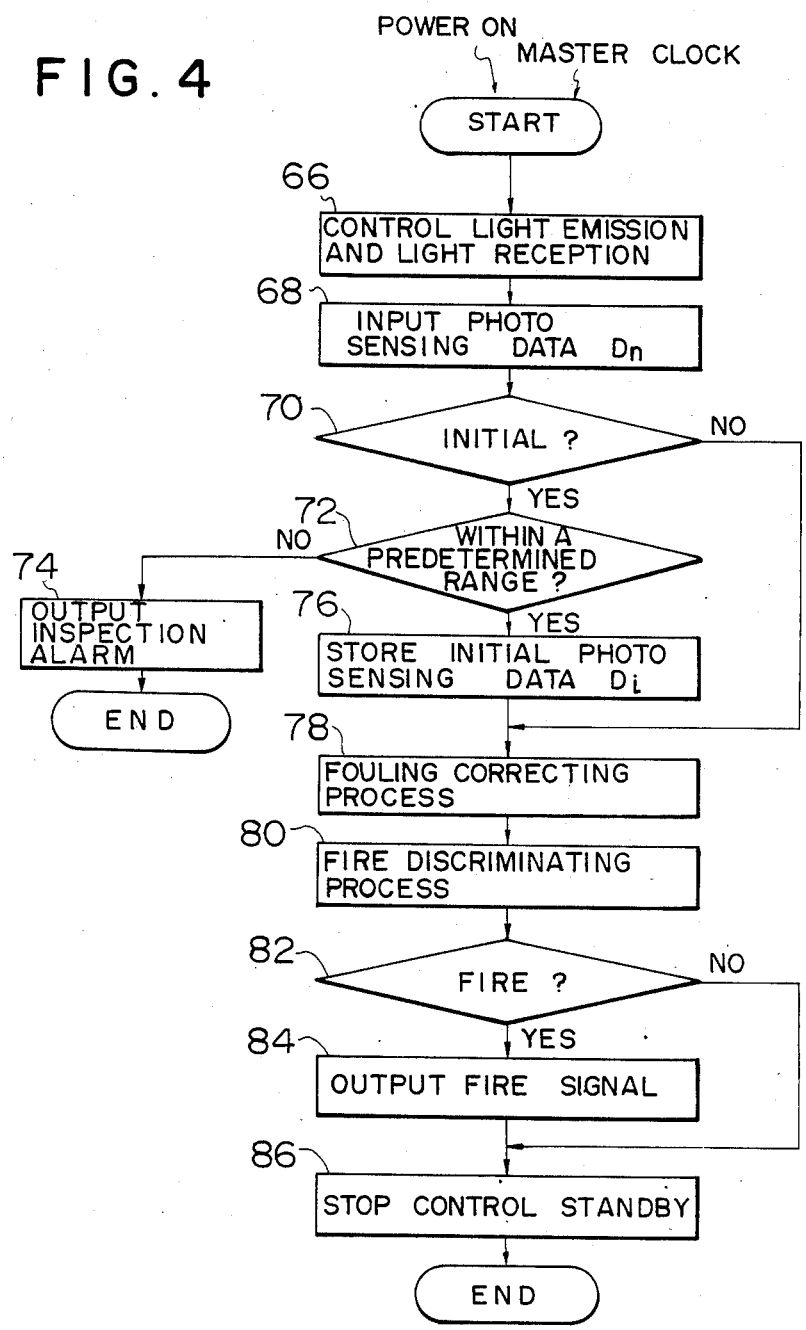
FIG. 4 is a general flowchart showing the program control process of the receiving unit.

FIG. 4 is a flowchart showing the control process of the photo sensing unit by the microcomputer in the control unit 36 in FIG. 3.

When the power source is first turned on, the power on reset circuit 40 outputs a power on reset signal and the microcomputer in the control unit 36 starts the operation. The microcomputer then performs the light emission and light reception controls in block 66. The photo sensing signal is derived by the photo sensing circuit 52 of the photo sensing unit due to the light emission and light reception controls, so that the A/D converted photo sensing data $D_n$ is inputted in block 68. In the next discriminating block 70, a check is made to see if the system is in the initial state or not. When it is determined in block 70 that the system is in the initial state since the power on reset has been performed due to the turning-on of the power source, discriminating block 72 follows. In block 72, a check is made to see if the photo sensing data $D_n$ obtained first lies within a predetermined range or not. When it is determined that the first photo sensing data $D_n$ is out of this range, block 74 follows and a signal for inspection alarm is outputted to the receiver. Namely, when the photo sensing data $D_n$ derived immediately after the power source was turned on is out of the predetermined range, this means the case where, for instance, the level of the photo sensing signal is extremely low because the optical axis between the photo sensing unit and the light emitting unit is deviated. Therefore, the inspection warning is performed to readjust the optical axis. On the other hand, when the photo sensing data $D_n$ exceeds the predetermined range, it can be considered that the gain control of the amplifier or the like provided in the photo sensing circuit 52 is improper. In this case as well, the inspection warning for readjustment is likewise performed.

On the other hand, when the photo sensing data $D_n$ lies within the predetermined range, block 76 follows and the photo sensing data $D_n$ is stored as the initial photo sensing data $D_i$ in the memory 42 of the microcomputer. As described above, even if the power supply from the receiver is completely stopped, the initial photo sensing data $D_i$ stored in the memory 42 will be held and stored for a predetermined time interval due to the charges in the capacitor 34 provided for the constant voltage circuit 32, so that it is not erased due to the temporary cut off of the power source or the like.

After completion of the storage of the initial photo sensing data $D_i$, the process routine advances the fouling correcting process in block 78. This fouling correcting process will be explained further in detail with reference to a block diagram of FIG. 5 and a flowchart of FIG. 6.

In the fouling correcting process in block 78, the photo sensing data $D_n$ is multiplied by a correction ratio N to correct the attenuation of the light due to the foulings on the windows of the photo sensing unit and light emitting unit, thereby obtaining a correction photo sensing data $D_a$ in the same condition as that whereby the windows are not dirty.

In block 80, the correction photo sensing data $D_a$ obtained in the fouling correcting process in block 78 is compared with the threshold value operated on the basis of the initial photo sensing data $D_i$, thereby discriminating the fire. Practically speaking, the photo sensing data for fire discrimination is derived from the moving mean of a plurality of fouling correction data which are derived at every constant detection period based on the master clock. When the time interval while this photo sensing data is below a predetermined threshold value continues for a constant time duration, it is determined that the fire occurred. As the result of the fire discriminating process in block 80, when it is determined that the fire occurred in discriminating block 82, block 84 follows and the fire signal is outputted to the receiver. On the contrary, when it is determined that no fire occurs, the fire signal outputting process in block 84 is not performed but block 86 directly follows and the control is stopped and the microcomputer is returned to the standby mode. Then, the system waits until the next clock pulse is inputted.

Figure 5:
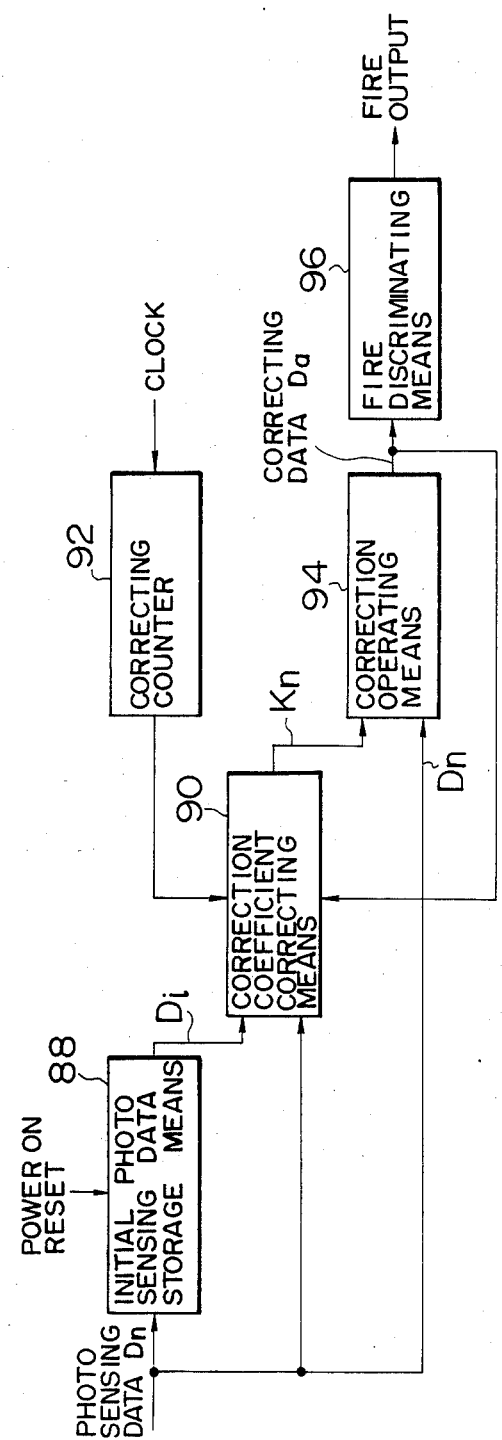
FIG. 5 is a function block diagram showing a processing circuit for the fouling correction according to the invention.

FIG. 5 is a block diagram showing the function of the microcomputer to execute the control processes in FIG. 4. This microcomputer is constituted by initial photo sensing data storage means 88, correction ratio correcting means 90, a correcting counter 92, correction operating means 94, and fire discriminating means 96.

Namely, the initial photo sensing data storage means 88 stores photo sensing data $D_m$ as the initial photo sensing data $D_i$ only at the time of power on reset due to the turning-on of the power source. In storage of the initial photo sensing data, it is obviously presumed that the photo sensing data lies within a predetermined range. The functions of the correction ratio correcting means 90, correcting counter 92 and correction operating means 94 will be further clearly understood due to the fouling correcting process with reference to a flowchart of FIG. 6. In addition, the correction operating means 94 performs the fouling correction to the photo sensing data $D_n$ derived by the light emission and light reception controls on the basis of the master clock and operates and outputs the correction data $D_a$ and supplies it to fire discriminating means 96.

Figure 6:
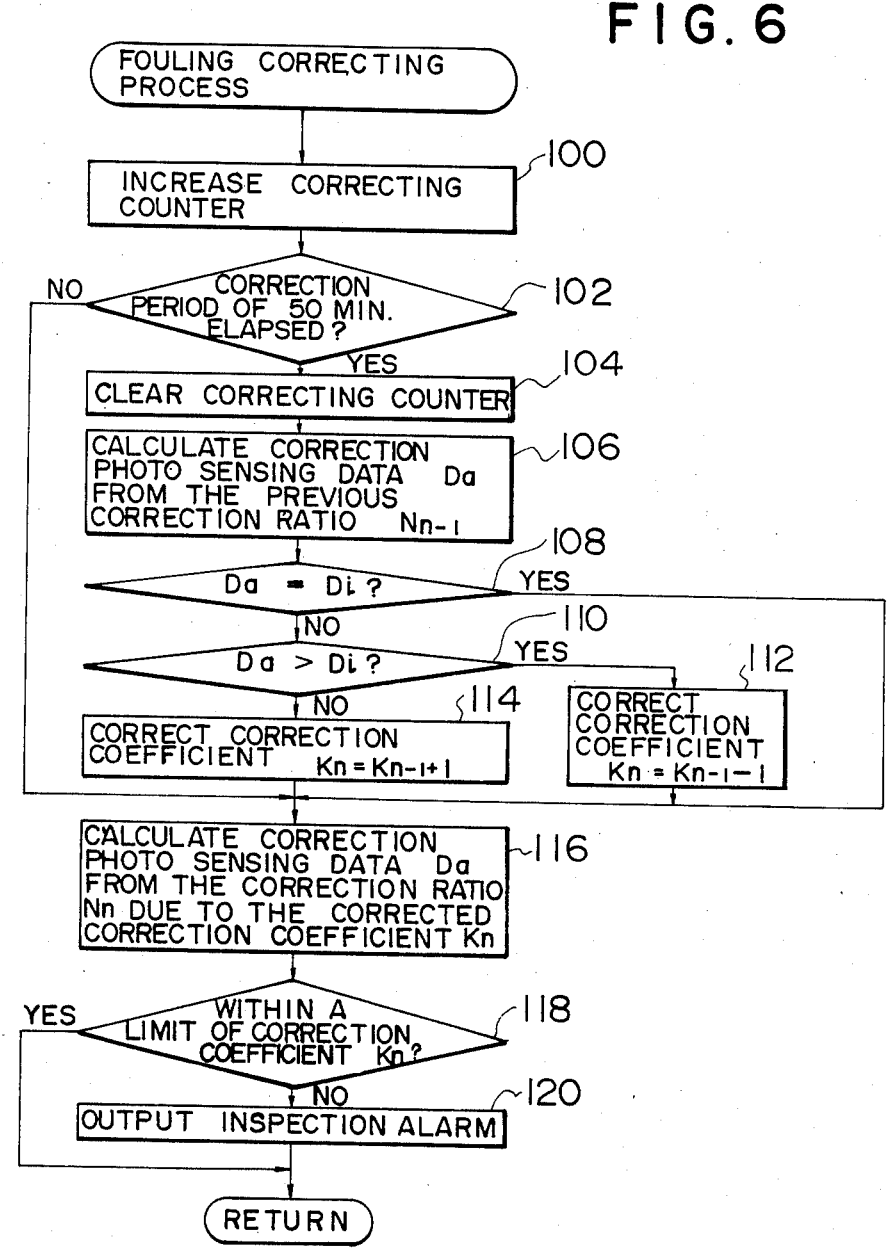
FIG. 6 is a flowchart showing the fouling correcting process of the receiving unit due to the program control.

FIG. 6 is a flowchart showing the fouling correcting process which is performed by the photo sensing unit in the photoelectric smoke sensor of the present invention. This fouling correcting process is executed by the program control of the microcomputer constituting the control unit or by the function block for the fouling correcting process consisting of the correction ratio correcting means 90, correcting counter 92 and correction operating means 94 shown in FIG. 5.

The fouling correcting process of FIG. 6 will now be described. First, the correcting counter is increased in block 100. This correcting counter can be realized by a program counter. The correcting counter counts a master clock which is outputted at a constant period within a range of, e.g., 2.7 to 3.0 seconds and reaches the full count in the count time interval of about 50 minutes and generates a counter output to execute the fouling correcting process. Namely, the count value of the correcting counter is monitored in discriminating block 102. When the count time of the counter reaches 50 minutes as the correcting period, the correcting process in block 104 and subsequent blocks is started.

The principle of the fouling correcting process to be executed in the processes in block 104 and subsequent blocks will then be explained hereinbelow.

When it is now assumed that the present photo sensing data derived by the light emission and light reception controls based on the clock pulse is $D_n$ and the correction ratio at this time is N, the correction photo sensing data $D_a$ will be obtained by $$D_a = D_n \times N \qquad \ldots (1)$$

The correction ratio N in equation (1) is defined by $$N = 1/(1 - K/100) \qquad \ldots (2)$$

Where, K is a correction coefficient and $K=0$ in the initial state. With a decrease in photo sensing data due to the fouling, the correction coefficient K sequentially increases at every correction period such that $K=1,2,3, \ldots$. On the contrary, as the photo sensing data increases, the correction coefficient K similarly has a value which sequentially decreases at every correction period such that $K=-1, -2, -3, \ldots$. Namely, in the case where the initial photo sensing data $D_i$ and the present photo sensing data $D_n$ do not coincide, the correction coefficient K is increased or decreased by only $\pm 1$ at every correction period, thereby correcting the correction ratio N.

The fouling correcting process in block 104 and subsequent blocks will then be practically described. First, the correcting counter is cleared in block 104. Next, in block 106, the correction photo sensing data $D_a$ is calculated from the previous correction ratio $N_{n-1}$ and the present photo sensing data $D_n$ by the foregoing equation (1).

After the correction photo sensing data $D_a$ was calculated in block 106, discriminating block 108 follows and a check is made to see if the correction photo sensing data $D_a$ is equal to the initial photo sensing data $D_i$ or not. At this time, if the windows are not dirty, $D_a = D_i$. However, if they are dirty, the correction photo sensing data $D_a$ becomes smaller than the data $D_i$, so that the process routine advances to discriminating block 110. In block 110, the magnitudes of the correction photo sensing data $D_a$ and initial photo sensing data $D_i$ are compared. In the case where the correction photo sensing data $D_a$ is larger than the initial photo sensing data $D_i$ in the comparing discrimination in this discriminating block 110, block 112 follows and the correcting process of the correction coefficient to correct the correction coefficient $K_n$ to a small value in order to reduce the correction ratio N is performed. That is, when $D_a > D_i$, the correction photo sensing data $D_a$ larger than the initial photo sensing data $D_i$ is calculated since the previous correction ratio $N_{n-1}$ used in the operation of the correction photo sensing data $D_a$ in block 106 is too large. Therefore, in block 112, the newly corrected correction coefficient $K_n$ is operated by setting such that $$K_n = K_{n-1} - 1 \qquad \ldots (3)$$

On the contrary, when it is determined that $D_a < D_i$ in discriminating block 110, block 114 follows and the new correction coefficient $K_n$ corrected by $$K_n = K_{n-1} + 1 \qquad \ldots (4)$$

is calculated. In case of the correction of the correction coefficient in block 114, $D_a < D_i$ since the previous correction ratio $N_{n-1}$ used in the calculation of the correction photo sensing data $D_a$ in block 106 is too small, so that the fouling correction lacks. Therefore, the new correction coefficient $K_n$ of which the correction coefficient $K_{n-1}$ was increased by only $+1$ by the foregoing equation (4) is derived. This increase of the $K_n$ causes a value of the correction ratio N which is obtained in the foregoing equation (2) to be also increased.

Change amounts of the correction coefficient K due to a single correction in blocks 112 and 114 are $\pm 1$; therefore, a change in correction ratio is also suppressed to a microvalue.

After the new correction coefficient $K_n$ was calculated in block 112 or 114, next block 116 follows and the correction photo sensing data $D_a$ is again calculated using the correction coefficient $K_n$ after correction on the basis of the foregoing equations (1) and (2).

Namely, when a correction is made such that $K_n = K_{n-1} + 1$ since $D_a < D_i$, the correction ratio N also increases and the correction photo sensing data $D_a$ which is further close to the initial photo sensing data $D_i$ is calculated. On the contrary, when a correction is made such that $K_n = K_{n-1} - 1$ since $D_a > D_i$, the correction ratio N also decreases, so that the correction photo sensing data which is closer to the initial photo sensing data $D_i$ is likewise calculated.

Subsequently, in discriminating block 118, a check is made to see if the new correction coefficient $K_n$ corrected in block 112 or 114 lies within a predetermined limit or not.

As one embodiment, the range where the correction coefficient $K_n$ varies is restricted to a range of $$+50 > K_n > -20 \qquad \ldots (5)$$

Therefore, when the correction coefficient $K_n$ reaches 50 or $-20$ as the result of correction of the correction coefficient $K_n$ at every correction period, a value of $K_n$ is out of the range of equation (5). Thus, it is determined that the fouling correction due to the signal process cannot be performed and the process routine advances to block 120 and a signal for inspection alarm is outputted to the receiver, thereby instructing the cleaning of the fouling attached onto the windows of the light emitting and photo sensing units.

This fouling correction shown in the flowchart of FIG. 6 will now be explained hereinbelow by use of practical numeric values.

It is now assumed that the initial photo sensing data $D_i$ equals 100 and the photo sensing data $D_n$ obtained at the present correction period is 95 and the previous correction coefficient $K_{n-1}$ is 0.

The correction data $D_a$ which is calculated in block 106 equals $D_n = 95$ from the foregoing equations (1) and (2) because the correction coefficient $K_{n-1}$ is 0.

Since the correction photo sensing data $D_a$ is smaller than the initial photo sensing data $D_i$, block 114 follows. In block 114, the correction coefficient is corrected by setting $K_n = K_{n-1} + 1 = 0 + 1 = 1$.

Next, the correction photo sensing data $D_a$ is calculated using the correction coefficient $K_n = 1$ after the correction in block 116 as follows.

$$D_a = 95 \times \{1/(1-1/100)\} = 95.95$$

Assuming that the present photo sensing data $D_n = 95$ is similarly derived at the next correction period, the correction coefficient $K_n$ is corrected to 2 in block 114, so that $D_a = 95 \times \{(1-2/100)\} = 96.9$ is calculated in block 116.

In a similar manner as above, the correction coefficient $K_n$ increases at every correction period such that $K_n = 3, 4, 5, \ldots$.

Namely, to make the present photo sensing data $D_n = 95$ approach the initial photo sensing data $D_i$, the correction coefficient increases at every correction period such that $K_n = 0, 1, 2, 3, 4, 5$, so that the correction ratio N which is given by equation (2) increases such that $N = 1.00, 1.01, 1.02, 1.03, 1.04, 1.05$. Consequently, even if the present photo sensing data $D_n$ does not change to 95, the correction photo sensing data $D_a$ increases such that $D_a = 95.00, 95.95, 96.94, 97.94, 98.96, 100.00$. In this way, the correction photo sensing data coincides with the initial photo sensing data at the fifth correction period. As long as the relation of $D_a = D_i$ is maintained, the fouling correction is performed by use of the correction ratio $N = 1.05$ which is determined by the correction coefficient $K_n = 5$.

On the contrary, when the present photo sensing data $D_n$ exceeds the initial photo sensing data, the correction coefficient $K_n$ decreases at every correction period such that $K_n = 0, -1, -2, -3, \ldots$ due to block 112. Thus, the correction ratio N decreases such that N=1.00, 0.99, 0.98, 0.97, ..., thereby making the correction photo sensing data $D_a$ approach the initial photo sensing data $D_i$.

In operation of the correcting process in the actual program process, when it is assumed that the data consists of, e.g., eight bits, the operating process is executed by setting $$256D_a = 256\{D_n \times 1/(1 \times K_n/100)\}$$

In the flowchart of FIG. 6, the correction coefficient $K_n$ is increased or decreased by only $\pm 1$ at every correction period. However, if the change of the correction ratio N is a microvalue the correction coefficient may be changed by amounts such as $\pm 2$, $\pm 3$, .... The change value of this correction coefficient can be arbitrarily determined to a value within a range where it does not exceed the change of the photo sensing data in the fumigation fire.

In addition, although the present invention has been described with respect to the photoelectric smoke sensor of the extinction separation type, the invention can be also applied as it is to a photoelectric smoke sensor of the integration type in which the light emitting unit and photo sensing unit of the invention are integrally provided in one chamber.

What is claimed is:

1. A photoelectric smoke sensor in which a light emitting unit and a photo sensing unit are arranged to face each other a predetermined distance away from each other, wherein a pulse light emitted from said light emitting unit, which has been attenuated due to smoke, is received by said photo sensing unit, thereby detecting a fire, comprising:

a storage means for storing photo sensing data when a power source is turned on as initial photo sensing data;

a correction ratio correcting means for comparing at every predetermined fouling correction period the photo sensing data at that time with said initial photo sensing data and, when a difference is noted between said data, for correcting a correction ratio in accordance with said difference;

a correction operating means for inputting the photo sensing data that is derived at every predetermined period shorter than said correction period as is and for obtaining correction photo sensing data due to a multiplication with the correction ratio at that time used as a multiplier; and a smoke discriminating means for discriminating a fire on the basis of said correction photo sensing data 2. A photoelectric smoke sensor according to claim 1, wherein said correction ratio correcting means has means for correcting the correction ratio by only a predetermined microvalue at the time of a single fouling correcting process.

3. A photoelectric smoke sensor according to claim 1, wherein said storage means has means for storing and holding said initial photo sensing data for a constant time interval even if the power source is turned off after the initial photo sensing data was stored.

4. A photoelectric smoke sensor according to claim 1, wherein said storage means has a data check means for determining whether or not said initial photo sensing data lies within a predetermined range and for storing said initial photo sensing data when it lies within said range and for generating an alarm when said initial photo sensing data is out of said range.

5. A photoelectric smoke sensor according to claim 1, wherein said fire discriminating means has a means for discriminating a fire by comparing a moving mean data of a plurality of correction photo sensing data outputted from said correction operating means with a threshold value.

* * * * *